United States Patent [19]

Targosz

[11] Patent Number: 5,658,954

[45] Date of Patent: Aug. 19, 1997

[54] WHITEFLY INSECTICIDE

[76] Inventor: Eugene F. Targosz, 1717 E. Union Hills Dr., Phoenix, Ariz. 85024

[21] Appl. No.: 593,230

[22] Filed: Jan. 29, 1996

Related U.S. Application Data

[62] Division of Ser. No. 214,828, Mar. 17, 1994, Pat. No. 5,496,857.

[51] Int. Cl.$^6$ .................. A01N 37/18; A01N 37/02
[52] U.S. Cl. .................. 514/617; 514/552; 514/555; 514/645; 424/DIG. 10
[58] Field of Search .................. 514/617, 552, 514/555, 645; 424/DIG. 10

[56] References Cited

U.S. PATENT DOCUMENTS

| | | | |
|---|---|---|---|
| 2,058,013 | 10/1936 | Henke et al. | 554/66 |
| 2,166,119 | 7/1939 | Bousquet | 514/627 |
| 2,173,909 | 9/1939 | Kritchevsky | 209/166 |
| 2,843,612 | 7/1958 | Ricclardi et al. | 554/66 |
| 2,863,888 | 12/1958 | Schruman | 554/66 |
| 2,877,246 | 3/1959 | Schurman | 554/66 |
| 3,040,075 | 6/1962 | Lohr | 554/66 |
| 3,257,436 | 6/1966 | Lindner | 554/66 |
| 3,257,437 | 6/1966 | Lindner | 554/66 |
| 3,422,021 | 1/1969 | Roy | 252/161 |
| 3,770,783 | 11/1973 | Henrick et al. | 554/66 |
| 3,995,059 | 11/1976 | Funkumaru et al. | 424/324 |
| 4,118,404 | 10/1978 | Nelson | 554/66 |
| 4,330,339 | 5/1982 | Nimerick | 106/243 |
| 4,597,895 | 7/1986 | Bartlett | 252/392 |
| 4,933,371 | 6/1990 | Hink et al. | 514/739 |
| 4,997,592 | 3/1991 | Woogerd | 252/307 |
| 5,292,504 | 3/1994 | Cardin et al. | 424/70 |

*Primary Examiner*—John W. Rollins
*Attorney, Agent, or Firm*—Thomas W. Tolpin

[57] ABSTRACT

A specially formulated environmental insecticide is provided which effectively controls whiteflies and other insects but is safe to humans, farm animals, pets, crops, and fish. The cost-effective non-polluting insecticide can be in the form of a 100% concentrate or an aqueous solution. The sprayable easy-to-use insecticide can comprise a synergistic blend of cottonseed oil amides, coconut oil amides, tall oil amides and a nonionic surfactant, as well as a chelating agent, a viscosity control agent and free amine.

18 Claims, No Drawings

1

WHITEFLY INSECTICIDE

This is a division of application Ser. No. 08/214,828, filed Mar. 17, 1994, now U.S. Pat. No. 5,496,857.

BACKGROUND OF THE INVENTION

This invention pertains to insecticides and, more particularly, to an insecticide for controlling whiteflies.

Whiteflies have caused extensive damage to food and fiber crops in Texas, Florida, California and Arizona. They attack some 500 crop and other plant species as well as poinsettias and other ornamentals. The sweet potato whitefly has been a major pest to many agronomic crops such as cotton, watermelon and cantaloupe. The whitefly also attacks area landscape by overwhelming plantings of lantana and passion vine. Arizona's long growing season along with a extensive list of suitable hoists for sweet potato whitefly make this pest extremely dangerous to agronomic and horticultural plantings. Crops attacked by whiteflies in the U.S.A. include: cotton, alfalfa, carrots, peanuts, cantaloupe, citrus, eggplant, honeydew melon, broccoli, cabbage, lettuce, celery, peppers, and vegetables.

As if California growers, who are periodically attacked by the Mediterranean fruit fly, didn't have enough to fret about, in the past two years along came another winged peril. A new type of whitefly, *Bemisia tabaci*, swirled like massive clouds of dandruff across fields of melons, lettuce, broccoli, and other vegetables. The pest was dubbed the poinsettia strain of the sweet potato whitefly in Florida, when it was sighted on ornamental plants. In California, the numbers went from troublesome to devastating in recent growing seasons. Pesticides and other remedies failed. People were even trying to vacuum the insects off their plants. Crop damage totaled 118 million dollars, 2,200 jobs were lost, and a state of emergency was declared in Imperial and Riverside Counties, because of whiteflies.

Populations of *Bemesia tabaci* whiteflies remain relatively light throughout the winter months due to their low fecundity during cooler months of the year but as the temperature rises crops like cantaloupe are planted in the spring and populations of Bemesia whiteflies begin to rise. As the spring melons are harvested the adult whitefly populations begin their migration to cotton where whiteflies mate. Females whiteflies lay their eggs on the underside of cotton leaves. Without grower intervention 6 to 12 generations of whitefly can be produced in a single growing season.

Successful control of sweet potato whitefly depends on destruction of the whitefly hosts. Whitefly control depends on the assistance of farmers and growers in an agronomic environment and the assistance of gardeners and homeowners in towns, cities and suburbs. Since cotton and vegetables are important crops to the agricultural economy, it is unlikely that either crop will be abandoned in an attempt to reduce the host range of the whitefly.

Many types of insecticides have been used to kill whiteflies and other insect pests with varying degrees of success. Unfortunately, conventional insecticides often pollute the atmosphere, create toxic waste, are not biodegradable, and contaminate rivers, streams, ponds, lakes, the ground, soil, and underground aquifers. Conventional insecticides can also damage crops, gardens, lawns, trees and shrubs. Furthermore, conventional insecticides can be hazardous to food supplies and can be harmful and even toxic to humans, animals, birds and fish.

It is, therefore, desirable to develop an improved insecticide which overcomes most, if not all, of the preceding problems.

SUMMARY OF THE INVENTION

An improved ecologically safe insecticide is provided which is toxic to insects but is nontoxic to and can safely contact humans, pets, farm animals, crops, trees, flowers, shrubs, gardens, birds, fish and other marine life. The insecticide can be: 100% active, biodegradable and carried propelled or sprayed by water. Advantageously, the environmentally attractive insecticide is effective, dependable and economical.

The user friendly insecticide is particularly useful to destroy, kill and control whiteflies. It can also be useful to destroy, kill or control other insects and pests, such as: spider mites, aphids, flea beetles, leaf hoppers, grasshoppers, houseflies, mosquitoes, diptera, homoptera, hemiptera, lepidoptera, coleoptera, mealybugs, rose slugs, scales, thrips, gnats, armyworms, bagworms, weevils, budworms, cankerworms, gypsy moths, Japanese beetles, leafminers, pine tip moths, webworms, and leaf-eating caterpillars.

The easy to use insecticide provides an insect-resistant protective agent and coating which can be useful to protect: cotton, watermelon, cantaloupe, honeydew melon, vegetables such as carrots, eggplants, broccoli, cabbage, lettuce, celery peppers, squash, cauliflower, tomatoes, cucumbers, sweet potatoes, corn, alfalfa, wheat, citrus, flowers and ornamentals such as poinsettias, dahlias, dogwood, roses, carnations chrysanthemums, geraniums, gladiolus, and marigolds, as well as shrubs, trees and grass (lawns).

To this end, the novel insecticide comprises an insecticidal surfactant and an insecticidal oil containing amide which provides a stomach poison for leaf-eating insects, a contact insecticide for sucking insects, a systemic insect control agent and/or a fly insecticide. The surfactant preferably comprises a nonionic surfactant for best results. In some circumstances it may be useful to use other surfactants, such as: an anionic surfactant, a cationic surfactant, an ampholytic surfactant or a zwitterionic surfactant. In the preferred form, the surfactant comprises: a wax-stripping surfactant, soap or detergent for stripping wax and oil from insects, an insect-suffocating wetting agent to suffocate insects, and a penetrate to penetrate and kill insect eggs and nymphs.

Carriers are useful to spray the whitefly insecticide. While an aqueous carrier is preferred for environmental compatibility and compliance, in some circumstances it may be desirable to use a non-aqueous hydrophobic liquid or solid carrier, such as: hydrocarbon oil, mineral oil, silica, talc, resin, xylene, benzene, toluene, acetone, methane, propane, acetylene, ethane, ethylene, butane, butylene, pentane, or other petroleum based liquids, cottonseed oil, coconut oil, vegetable oil, seed oil, nut oil, fish oil or animal oil. The amides can be applied in conjunction with one or more liquids, semi-liquids or solid insecticidal or non-insecticidal substances and carriers.

For best results, the insecticidal oil-containing amides comprise a synergistic blend of cottonseed oil amide, coconut oil amide and tall oil amide. In some circumstances, it may be desirable that the insecticidal oil-containing amides comprise reaction products of amines or fatty acids reacted with one or more of the following oils: corn oil, castoroil, palm oil, palm kernel oil, soybean oil, cottonseed oil, coconut oil, tall oil, lard oil, oleic oil, rape oil, linseed oil, olive oil, peanut oil, fish oil, soybean oil, sesame oil, hemp seed oil, perilla oil, styrax oil, oiticica oil, kayo oil, walnut oil, cashew oil, poppy seed oil, safflower oil, watermelon seed oil, sunflower oil, rice bran oil, pumpkin seed oil, tsubaki oil, crystalis oil, kaoliang oil, ergot oil, bone oil, shark oil, sardine oil, pike oil, herring oil, saurel oil, cod oil, cuttlefish oil, trout oil, mullet oil, tuna oil, menuke oil, menhadden oil, eel oil, whale oil, liver oil, chinawood oil, plant oil, vegetable oil and animal oil.

The amines can comprise alkanolamines, such as: monoethanolamine, diethanolamine, monoisopropanolamine, diisopropanolamine, monopropanolamine, dipropanolamine, monobutanolamine, dibutanolamine, monopentanolamine, dipentanolamine, monohexanolamine, dihexanolamine, monoethanolamine, methoxypropan-ol-3; 2-N-methylaminopropandiol-1,3; monoethanol monopropanolamine; monoethanol monobutanolamine; alkylol polyamines such as alkylol derivatives of ethylene diamine, diethylene triamine, and triethylene tetra-amine, such as hydroxy ethyl ethylene diamine, diglycerol monoamine, deglyceroldi-amine, hydroxy-alkyl amines derived from other polyhydric alcohols, including glycols, sugars and sugar alcohols such as ethylene glycol, diethylene glycol, glycerol, dextrose, sucrose, sorbitol, mannitol and dulcitol. Other suitable amines include diisopropanol amine and monoisopropanol amine.

The inventive technology has produced unexpected surprisingly good results. Tests show the insecticide to be very useful to control and destroy whiteflies without being injurious to people, animals, plants and fish, and without contaminating the atmosphere, ground, streams, rivers, ponds, lakes, etc.

A more detailed explanation of the invention is provided in the following description and claims.

DETAILED DESCRIPTION OF THE PREFERRED EMBODIMENTS

A whitefly insecticide is provided to kill, destroy or otherwise control sweet potato whiteflies (*bemesia abaci*), as well as other flies and insects. Desirably the whitefly insecticide is poisonous and toxic to sweet potato whiteflies and other flies and insects, but is safe and non-toxic to breathe or contact humans, farm animals, pets, game, birds, fish, crops, gardens, lawns and flowers. Advantageously, the whitefly insecticide does not pollute the atmosphere, soil, streams, ponds, lakes, rivers, or underground aquifers.

The preferred whitefly insecticide comprises a 100% active, biodegradable, environmentally safe insecticidal concentrate which can also be sprayed from an aqueous solution. The concentrate can comprise by weight: 1% to 50% nonionic surfactants, oil-containing alkanolamides comprising 1% to 50% cottonseed oil amide, 1% to 40% coconut oil amide, 1% to 20% tall oil amide, 1% to 5% chelating agent, 1% to 10% viscosity control agent, and 1% to 10% free (excess) alkanol amine. The ratio of water in the aqueous solution to concentrate can range from 10,000:1 to 200:1. The nonionic surfactants can comprise phenol ethoxylates comprising a condensate product of ethylene oxide and an alkyl phenol or an aliphatic alcohol.

The oil-containing alkanol amides can comprise one or more of the following alkanol amides: monoethanolamide, diethanolamide, triethanolamide, monopropanolamide, dipropanolamide, isopropeanolamide, monobutanolamide, monoisobutamide, monoisobutanolamide, dibutanolamide, monopentanolamide, dipentanolamide, monohexanolamide, cyclohexanolamide. The free alkanolamine are to bias or force reaction to the right to produce amides and prevent separation. The free alkanolamines can comprise one of the following olamine-containing compounds: monoethanolamine, diethanolamine, triethanolamine, monopropanolamine, dipropanolamine, isopropanolamine, dipropanolamine, isopropanolamine, monobutanolamine, monoisobutanolamine, dibutanolamine, monopentanolamine, dipentanolamine, dioctanolamine, and cyclohexanolamine.

Preferably, the whitefly insecticidal concentrate comprises by weight: 25% to 40% nonionic surfactants, oil-containing ethanol amide comprising 25% to 40% cottonseed oil amide, 10% to 35% coconut oil amide, and 2% to 15% tall oil amide, 2% to 8% viscosity control agent, 1% to 4% chelating agent, and 2% to 8% excess free hydroxylkylamine, such as monoethanolamine, diethanolamine and/or triethanolamine. The oil-containing amides preferably comprise monoethanolamide, diethanolamide and/or triethanolamide. The oil-containing amides are reaction products of the above named hydroxylalkylamines and cottonseed oil, coconut oil and tall oil. A catalyst can be used, if desired. The ratio of the oils to the hydroxyalkyamines can range from 3:1 to 0.5:1 preferably from 2.5:1 to 1.5:1 and most preferably about 1:1. The nonionic surfactants preferably comprise nonophenol ethoxylate such as T-DET, and/or octaphenol ethoxylate. The nonionic surfactants are reaction products of ethylene oxide and nonolphenol and/or octaphenol. The ratio of the phenol to the ethylene oxide can range from 2:20 to 4:16 and preferably is about 8:12. Where aqueous sprays, carriers, propellants, or solutions are used, the ratio of water to the concentrate can range from 6000:1 to 500:1.

For best results, the white fly insecticidal concentrate comprises by weight: 32% to 35% nonionic surfactants, 32% to 35% cottonseed oil amide, 15% to 28% coconut oil amide, 5% to 10% tall oil amide, 3% to 5% viscosity control agent, 2% to 3% chelating agent, and 3% to 5% excess free hydroxyalkylamine. Preferably, the amides (ethanol amides) comprise diethanolamides, the viscosity control agent comprises sodium xylene sulfonate, the chelating agent comprises a tetrasodium salt of ethylene diamine tetracedic acid, and the hydroxyalkylamine comprises diethanolamine. Where water or water-based sprays, carriers, propellants, or solutions are used, the ratio of water to the concentrate can range from 1200:1 to 800:1, and is preferably about 1000:1.

The viscosity control agents lowers and maintains the viscosity of the concentrate and helps stabilize the emulsion of amides. The chelating agents help prevent the surfactant (soap) from curdling, coagulating and blocking the spray nozzle.

While the above compounds are preferred for the most effective biodegradable environmentally safe insecticide, in some circumstances it may be desirable to use other amides, viscosity control agents, chelating agents, and amines.

Nonionic Surfactant

The nonionic surfactants are preferred because they provide effective insecticidal wetting agents which penetrates whitefly eggs, nymphs, suffocates adult whiteflies, strips the protective wax and oily coating off the bodies of whiteflies, and drown the whiteflies.

Nonionic surfactants are surface-active compounds which do not ionize in water solution. Often times these possess hydrophilic characteristics by virtue of the presence therein of an oxygenated chain (e.g., a polyoxyethylene chain), the lyophilic portion of the molecule being derived from fatty acids, phenols, alcohols, amides or amines. Exemplary compounds are the poly-(ethylene oxide) condensates of alkyl phenols, e.g. the condensation product formed from one mole of nonyl phenol and ten moles of ethylene oxide, and the condensation products of aliphatic alcohols and ethylene oxide, e.g. the condensation product formed from 1 mole of tridecanol and 12 moles of ethylene oxide.

The nonionic surfactants can comprise phenol ethoxylates comprising a condensate product of ethylene oxide and an alkyl phenol or an aliphatic alcohol. The nonionic surfactants preferably comprise nonophenol ethoxylate such as T-DET, and/or octaphenol ethoxylate. The nonionic surfactants are reaction products of ethylene oxide and nonolphenol and/or octalphenol. The ratio of the phenol to the ethylene oxide can range from 2:20 to 4:16 and preferably is about 8:12.

Nonionic synthetic surfactants can comprise nonionic detergents. Nonionic synthetic surfactants can also be formed by condensing ethylene oxide with a hydrophobic base formed by the condensation of propylene oxide with propylene glycol. The hydrophobic portion of the molecule which, of course, exhibits water insolubility has a molecular weight of from about 1200 to 2500. The addition of polyoxyethylene radicals to this hydrophobic portion tends to increase the water solubility of the molecule as a whole and the liquid character of the product can be retained up to the point where polyoxyethylene content is about 50% of the total weight of the condensation product.

Other nonionic synthetic surfactants can include: the polyethylene oxide condensates of alkylphenols, e.g. the condensation products of alkylphenols or dialkylphenols wherein the alkyl group contains from about 6 to 12 carbon atoms in either a straight chain or branched chain configuration, with ethylene oxide. The ethylene oxide can be present in amounts equal to 8 to 25 moles of ethylene oxide per mole of alkylphenol. The alkyl substituent in such compounds can be derived from polymerized propylene, diisobutylene, n-octene, or n-nonene.

Nonionic surfactants can also be produced from the condensation of ethylene oxide with the reaction product of propylene oxide and ethylenediamine, e.g. compounds containing from about 40% to about 80% polyoxyethylene by weight and having a molecular weight of from about 5,000 to about 11,000 resulting from the reaction of ethylene oxide groups with a hydrophobic base comprising the reaction product of ethylenediamine and excess propylene oxide; the base having a molecular weight on the order of 2,500 to 3,000.

Other nonionic surfactants include the condensation product of aliphatic alcohols having from 8 to 18 carbon atoms, in either straight chain or branched chain configuration, with ethylene oxide, e.g. a coconut alcohol ethylene oxide condensation having from 10 to 30 moles of ethylene oxide per mole of coconut alcohol, and the coconut alcohol fraction having from 10 to 14 carbon atoms.

Further nonionic surfactants include long chain tertiary amine oxides corresponding to the following general formula:

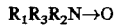

wherein R1 is an alkyl radical of from about 8 to 18 carbon atoms, and $R_2$ and $R_3$ are each methyl or ethyl radicals. The arrow in the formula is a conventional representation of a semi-polar bond. Examples of amine oxides suitable for use include: dimethyldodecylamine oxide, dimethyloctylamine oxide, dimethyldecylamine oxide, dimethyltetradecylamine oxide, and dimethylhexadecylamine oxide.

Other nonionic surfactants can include: long chain tertiary phosphine oxides corresponding to the following general formula

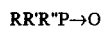

wherein R is an alkyl, alkenyl or monohydroxyalkyl radical ranging from 10 to 18 carbon atoms in chain length and R' and R" are each alkyl or monohydroxyalkyl groups containing from 1 to 3 carbon atoms. The arrow in the formula is a conventional representation of a semi-polar bond. Examples of suitable phosphine oxides are: dimethyldodecylphosphine oxide, dimethyltetradecylphosphine oxide, ethylmethyltetradecylphosphine oxide, cetyldimethylphosphine oxide, dimethylstearylphosphine oxide, cetylethylpropylphosphine oxide, diethyldodecylphosphine oxide, diethyltetradecylphosphine oxide, dipropyldodecylphosphine oxide, bis-(2-hydroxymethyl)dodecylphosphine oxide, bis-(2-hydroxyethyl)dodecylphosphine oxide, (2-hydroxypropyl)methyltetradecylphosphine oxide, dimethyloleylphosphine oxide, and dimethyl-(2-hydroxydodecyl)phosphine oxide.

Other Surfactants

While nonionic surfactants are preferred for best results, in some circumstances it may be useful to use other surfactants in the insecticide, such as: an anionic surfactant, a cationic surfactant, an ampholytic surfactant or a zwitterionic surfactant.

The anionic surfactants comprise surface-active compounds. The anionic surfactants can contain hydrophilic and lyophilic groups in their molecular structure which ionize in an aqueous medium to give anions containing the lyophilic group. Typical of these compounds are the alkali metal salts of organic sulfonates or sulfates, such as the alkali metal alkyl aryl sulfonates and the alkali metal salts of sulfates of straight chain primary alcohols. Sodium dodecylbenzene sulfonate and sodium lauryl sulfate are typical examples of these anionic surface-active compounds.

Anionic surfactants can comprise synthetic detergents. Anionic surfactants can include: sodium alkyl sulfates, especially those obtained by sulfating the higher alcohols (C8–C18 carbon atoms) produced by reducing the glycerides of tallow or coconut oil; sodium alkylglycerylethersulfonates, especially those ethers of the higher alcohols derived from tallow and coconut oil; sodium coconut oil fatty acid monoglyceride sufates and sulfonates; the reaction product of fatty acids esterified with isethionic acid and neutralized with sodium hydroxide, where, for example, the fatty acids are derived from coconut oil; sodium or potassium salts of fatty acid amide of a methyltauride in which the fatty acids are derived from coconut oil.

One anionic fluorochemical surfactant or a fluorocompound wetting agent, comprises: 37.5% 2-butoxyethanol, 37.5% water, and less than 30% ammonium perfluoroalkyl sulfonate, with a boiling point of approximately 96 degrees C. a vapor pressure of 27.2 mm/Hg, a vapor density of about 0.7, a pH of 8.5–9.5, and is 75% volatile, such as sold under the FLUORAD brand name of FC-120 by 3M Company, St. Paul, Minn., U.S.A.

Other anionic fluorosurfactants or fluorocompound wetting agents which can be used include those sold by 3M Company under the FLUORAD brand names FC-109, FC 121, FC-129 and FC-170C, or fluorosurfactants sold by E. I. Du Pont de Nemours & Company of Wilmington, Del., U.S.A. under the ZONYL brand names FSP, FSE, FSE, FSJ, FSN, FSN-100, FSO, FSO-100, FSC, and TBS. Fluorsurfactants can be used alone or with a hydrocarbon surfactant.

The surfactant FC-109 is an anionic fluorochemical surfactant comprising: 61% water, 12% dipropylene glycol monomethyl ether, 2% ethanol, and 25% potassium fluoralkyl carboxylates, with a boiling point of approximately 173 degrees F., a vapor pressure of about 30 mm/Hg, a vapor density of less than 0.6%, a specific gravity of approximately 1.1, a pH of 8–11, and a volatility of about 75%. FC-121 is an anionic fluorochemical surfactant comprising:

40% water, 35% propylene glycol monotertiary butyl ether, and 25% ammonium perfluoroalkyl sulfonates, with a boiling point of about 212 degrees F., a vapor pressure of 28 mm/Hg, a vapor density of 0.7, a specific gravity of approximately 1.1, a pH of 8.5–9.5, and a volatility of approximately 75%. FC-129 is an anionic fluorochemical surfactant comprising: 32% water, 14% 2-butoxy-ethanol, 4% ethanol, and less than 40% potassium fluoralkyl carboxylate, with a boiling point of approximately 212 degrees F., a vapor pressure of about 28 mm/Hg, a vapor density of about 0.7, a specific gravity of approximately 1.3, a pH of about 8–11, and is approximately 50% volatile. FC-170C is a fluorochemical surfactant comprising: approximately 70% fluoroaliphatic oxyethylene adduct, 12% polyoxyetheylene glycol, a maximum of 7% water, with a boiling point of about 210 degrees C., a vapor pressure of 31 mm/Hg, a vapor density of 0.61, a specific gravity of 1.3, a pH of 6–8, and a volatility of about 7%.

ZONYL FSK is a fluorinated surfactant comprising: 53% acetic acid, 47% polytetrafluoroethylene (PTFE) alpha-(2-acetoxy-3-(carboboxymethyl) dimethylammonio(propyl)-omega-fluoro-inner salt, has a boiling point of 118 degrees C. at 760 mm/Hg, a vapor density of 2.1, a specific gravity of 1.2 and is 53% volatile. ZONYL FSO is a fluorinated surfactant comprising: 50% telomer B monoether with polyethylene glycol, 25% ethylene glycol, 25% water, has a boiling point of 100 degrees C., a vapor density of 2.1, a specific gravity of 1.3 and is 50% volatile. ZONYL FSP is a fluorinated surfactant comprising: 20% isopropyl alcohol, 40–45% water and the balance telomer B phosphate ammonium salt, has a specific gravity of 1.15, a pH of 6–8, and is 65% volatile. ZONYL FSN is a fluorinated surfactant comprising: 40% telomer B monoether with polyethylene glycol, 30% isopropyl alcohol, 30% water, a boiling point of—80 degrees C. at 760 mm/Hg, a specific gravity of 1.06 a pH of 7.5–8.5 and is 60% volatile.

The cationic surfactants can include cationic detergents. The cationic surfactants comprise compounds which ionize in an aqueous medium to give cations containing the lyophilic group. Typical of these compounds are the quaternary ammonium salts which contain an alkyl group of about 12 to about 18 carbon atoms, such as lauryl benzyl dimethyl ammonium chloride.

Ampholytic surfactants are compounds having both anionic and cationic groups in the same molecule. Exemplary of such compounds are derivatives of aliphatic amines which contain a long chain of about 8 to about 18 carbon atoms and an anionic water solubilizing group, e.g., carboxysulfo, sulfo or sulfato. Examples of ampholytic detergents are: sodium-3-dodecylaminopropane sulfonate, sodium-N-methyl taurate, and related substances such as higher alkyl disubstituted amino acids, betaines, thetines, sulfated long chain olefinic amines, and sulfated imidazoline derivatives.

Zwitterionic surfactants can include synthetic detergents. Zwitterionic surfactants are generally derivatives of aliphatic quaternary ammonium compounds in which the aliphatic radical can be a straight chain or branched and wherein one of the aliphatic substituents contains from about 8 to 18 carbon atoms and one contains an anionic water solubilizing group, e.g., carboxy, sulfo, or sulfato. Examples of compounds falling within this definition are: 3-(N,N-dimethyl-N-hexadecyl ammonio)-propane-1-sulfonate and 3-(N,N-dimethyl-N-hexadecyl ammonio)-2-hydroxypropane-1-sulfonate.

Amides

A blend of cottonseed oil amides, coconut oil amides, and tall oil amides are preferred because they: provide a very affective nonionic stomach insecticide for whieflies and sucking insects, are economical, provide insecticidal emulsifiers, improve solubility and help successfully strip waxy surfaces from the whiteflies. Cottonseed oil amides provide an inexpensive reliable insecticide. Coconut oil amides improve solubility, i.e. helps prevent separation of the concentrate, and effectively coats and drowns whiteflies. Tall oil amides are also helpful to strip the wax off the bodies of whiteflies.

The preferred amides are oil-containing ethanolamides which comprise one or more of the following: monoethanolamide, triethanolamide, or preferably diethanolamide. The oil-containing ethanolamides are reaction products of cottonseed oil, coconut oil and tall oil with monoethanolamine, triethanolamine, and/or preferably diethanolamine. While the above oil-containing amides are preferred, other amides can be used in some circumstances, which comprise one or more of the following alkanolamides: monopropanolamide, dipropanolamide, isopropanolamide, monobutanolamide, monoisobutamide, monoisobutanolamide, dibutanolamide, monopentanolamide, dipentanolamide, monohexanolamide, and cyclohexanolamide.

In some circumstances, it may be desirable that the insecticidal oil-containing amides comprise one or more of the following amides: fatty acid hydroxyalkyl amide, alkanolamide, ethanolamide, isobutylamide, isopropylamide, n-dodecylamide, dimethylamide, alpha-naphthylamide, dicyclohexylamide, tetra-n-butylamide, di-n-butylamide, para-methoxy-phenylamide, tetrahydrofurylamide, thiodiphenylamide, dimorpholide, morpholide, n-hexylamide, n-dodecylamide, 5-ethoxy-benzthiazol-1-amide, and a carboxylic acid amide.

Other insecticidal oil-containing amides which can be used in preparing the whitefly insecticide, include: dimethylamide of lauric acid, the n-dodecylamide of lauric acid, the amide of lauric acid, the n-dodecylamide of lauric acid, the amide of lauric acid, the n-dodecylamide of formic acid, the isobutylamide of di-n-heptylacetic acid, and the isobutylamide of ethyl-n-butylacetic acid. Mixtures of amides can be also be used, such as: the isobutylamide of ethyl-n-butylacetic acid, the isobutylamides of linseed, olive, coconut, or Chinawood oil acids, and the isobutylamides of the acids obtained by oxidizing the mixture of alcohols of eight or more carbon atoms produced in the catalytic hydrogenation of the carbon oxides. The mixtures of fatty oil acid amides can be obtained by heating the oil or fat with ammonia or amines at superatmospheric pressures. Other butyl amides can also be used. The insecticidal oil-containing amides can be a reaction of fatty acids or fatty acid esters (i.e. esters of fatty acids) with amines.

Some suitable amides are: isobutylamide of octanole acid, isobutylamide of decanoic acid, isobutylamide of undecylenic acid, isobutylamide of oleic acid, isobutylamides of castor oil acids, isobutylamides of naphthenic acids, isobutylamides of acids obtained by oxidation of petroleum hydrocarbons, isobutylamide of ethyl-n-heptylacetic acid, isobutylamide of n-butyo-n-amylacetic acid, n-dodecylamide of isobutyric acid, N-dodecylamide of formic acid, isobutylamide of di-n-heptylacetic acid, the isobutylamide of ethyl-n-butylacetic acid, alpha-naphthylamide of lauric acid, n-dodecylamide of salicylic acid, piperidide of lauric acid, isobutylamide of thiolauric acid the n-dodecylamide of thioacetic acid, isobutylamide of thiocapric acid, isobutylamide of thiocapric acid, n-dodecylamide of thiobenzoic acid, n-dodecylamide of thiobenzoic acid, n-dodecylamide of thiobenzoic acid, di-cyclohexylamide of oleic acid, piperidide of thiolauric acid, and the amide of thiolauric acid.

Other suitable amides include: tetra-n-butylamide of phthalic acid and di-n-butyldiamide of phthalic acid, the para-methoxy-phenylamide of lauric acid, para-ethoxyphenylamide of lauric acid, para-ethoxyphenylamide of lauric acid, n-dodecylamide of alpha-picolinic acid, n-dodecylamide of furoic acid, the di-morpholide of sebasic acid, the di-morpholide of sebasic acid, the morpholide of lauric acid, the morpholide of undecylenic acid, the tetrahydrofurylamide of octanoic acid, thiodiphenylamide of lauric acid, the morpholide of oleic acid, decahydroquinolide of lauric acid, morpholides of Chinawood oil acids, morpholides of soya bean oil acids, morpholide of hexahydrophthalic acid, n-hexylamide of nicotinic acid, n-decylamide of tetrahydrofuroic acid, 5-ethoxy-benzthiazol-1-tetrahydrofuroic acid, 5-ethoxy-benzthiazol-1-amide of octanoic acid, 1-octanoyl-2-(3-pyridyl) piperidine, dimorpholide of suberic acid, dimorpholide of azelaic acid, the morpholide of ricinoleic acid, the morpholide of 12-hydroxystearic acid, and the amide of thiobenzoic acid.

Examples of reactants for producing suitable amides are the residues of following fatty acids: in the case of saturated acids, myristic acid, palmitic acid, stearic acid, isostearic acids, arachidic acid, behenic acid, lignoceric acid, cerotic acid and montanic acid; and in the case of unsaturated acids, residues of tsuzuic acid, physetoleic acid, myristoleic acid, zoomaric acid, palmitoleic acid, petroselinic acid, oleic acid, elaidic acid, vaccenic acid, gadoleic acid, erucic acid, brassidic acid, selacoleic acid, linoleic acid, linolenic acid, eleostearic acid, ricinoleic acid, parinaric acid, arachidonic acid, eicosatetraenoic acid, elcosapentaenoic acid, docosapentaenoic acid, hemp-seed oil fatty acid, linseed oil fatty acid, perilla oil fatty acid, styrax oil fatty acid, oiticia oil fatty acid, kayo oil fatty acid, walnut oil fatty acid, poppyseed oil fatty acid, safflower oil fatty acid, water melon-seed oil fatty acid, soybean oil fatty acid, sunflower oil fatty acid, rice bran oil fatty acid, pumpkin-seed oil fatty acid, kaoliang oil fatty acid, sesame oil fatty acid, corn oil fatty acid, rape oil fatty acid, rape oil fatty acid, cottonseed oil fatty acid, olive oil fatty acid, cashew oil fatty acid, tsubaki oil fatty acid, ergot oil fatty acid, castor oil fatty acid, peanut oil fatty acid, palm oil fatty acid, palm kernel oil fatty acid, coconut oil fatty acid, beef tallow fatty acid, lard fatty acid, bone oil fatty acid, horse fat fatty acid, locust oil fatty acid, crystalis oil fatty acid, shark oil fatty acid, cuttlefish oil fatty acid, sardine oil fatty acid, horse-mackerel oil fatty acid, mackerel oil fatty acid, saury pike oil cod oil fatty acid, trout oil fatty acid, gray mullet oil fatty acid, tunny oil fatty acid, menuke oil fatty acid, menhaden oil fatty acid, flatfish oil fatty acid, eel oil fatty acid, whale oil fatty acid, body oil fatty acid, skin oil fatty acid, head oil fatty acid, liver oil fatty acid, residual oil fatty acid and egg oil fatty acid and plant, land or marine animal oils.

Suitable fatty acid radicals of esters include: capric, lauric, myristic, palmitic, stearic, linoleic, oleic, arachidic and behenic acids and those acids derived from naturally occurring products such as coconut, palm kernel, babassu, palm, fish, linseed, sperm, soybean, olive, and cottonseed oils, grease, tallow, and their hydrogenation products.

The amides can be a reaction product of oils and higher organic acids or higher fatty acids having a chain of at least six carbon atoms. Fatty acids, derived from waxes, having as high as thirty-five carbon atoms or more can also be used. Examples of suitable acids, are the higher molecular weight saturated and unsaturated aliphatic and fatty acids including capric, caproic, caprylic, stearic acid, hydroxystearic acid, oleic acid, lauric acid, myristic acid, coconut oil mixed fatty acids, linoleic acid, rionoleic acid, palmitic acid, melissic acid; and mixed higher fatty, linoleic acid, palmitic acid, melissic acid; and mixed higher fatty acids derived from animal and vegetable oils and fats, whether hydrogenated or not, such as cottonseed oil, corn oil, soya bean oil, sesame oil, fish oils, lard, oleo oil, and others, such as the fatty acids derived from waxes like beeswax and carnauba wax. It will also be understood that the acids which are condensed with the alkylolamines need not necessarily be mono-basic acids. Di-basic and poly-basic acids can also be used, such as sebasic acid and Japanic acid. Cyclic acids, such as naphthenic acid, hydroaromatic acids such as abietic acid, and quinaldine-carboyxlic acid can also be used as well as aromatic acids such as benzoic, naphthoic and the like. It is not necessary to always use free acids, such as the free fatty acids, but it may be feasible and effective to use triglyceride oils or fats as a source of the higher fatty acids, in which case glycerine or other alcohols forming the fatty esters split off during the condensation. In some circumstances it may be desirable to use sulphonated and phosphated derivatives of oils or fats as well as sulfuric acid esters of oils or fats, like sulphonated castor oil.

Amines

The excess free olamine, preferably diethylanolamine, helps keeps the pH of the insecticide above 7 to provide an alkaline insecticide. The amines react with the tall oil and coconut oil to minimize separation of the amide emulsion, i.e. to prevent separate layers of the cottonseed oil amides, coconut oil amides and tall oil amides.

Other amines which can be used comprise alkylol-amines or hydroxyalkylamines, such as: monoethanolamine, diethanolamine, triethanolamine including commercial triethanolamine which contains small proportions of monoethanolamine and diethanolamine, diethyl-alkylolamine, monoethyl-alkylolamine, propanolamines, isopropanolamine, butanolamine, hexanolamine, cyclohexylethanolamine, the alkylolamines of glycerine, sugar, sugar alcohols such as sorbitol and mannitol, other mono- and poly-valent alcohols, and alkylol di- and poly-amines.

Suitable amidating agents include: hydroxy-alkyl amines which have an alkyl group joining at least one esterifiable hydroxy group to a nitrogen atom to which there is attached at least one replaceable hydrogen atom. Among the representative hydroxy-alkyl amines which can be used are, for example, monoethanolamine, monopropanolamine, dipropanolamine, dibutanolamine, monobutanolamine, monoisobutanolamine, mono- and dipentanolamine, mono- and dihexanolamine, mono- and dioctanolamine, monolaurylolamine, monohexadecylolamine, monoethylethanolamine, mono-octadecylolamine, monobutyl ethanolamine, cyclohexyl ethanolamine, ethanolaniline, 2-methyl-amine-propane-diol-1,3, 1-hydroxy-ethylamine-2, -methoxy-propan-ol-3 diglycerol monoamine, and diglycerol diamine.

Carriers

The whitefly insecticidal concentrate can be sprayed or otherwise applied using either liquid or solid carriers. Water is the preferred carrier for ecological reasons. The ratio of water in the aqueous solution to concentrate can range from 10,000:1 to 200:1, preferably from 6000:1 to 500:1, and most preferably from 1200:1 to 800:1, e.g. about 1000:1.

While an aqueous carrier is preferred for environmental compatibility and compliance, in some circumstances it may be desirable to use a non-aqueous hydrophobic liquid or solid carrier, such as: hydrocarbon oil, mineral oil, silica, talc, natural resins, synthetic resins, pyrethrum, talc, thiocyanates, phthalates, xylene, benzene, toluene, acetone, methane, propane, acetone, acetylene, ethane, ethylene, butane, butylene, pentane, kerosene, gasoline, or other petroleum based liquids, as well as cottonseed oil, coconut oil, pine oil, vegetable oil, seed oil, nut oil, fish oil or animal oil. The resulting composition may be a liquid a semi-liquid or a comminuted solid as needed and desired by appropriate selection of the amide and/or the carrier.

EXAMPLES

A greenhouse experiment was initiated on sweet potato whitefly to compare the efficacy of a registered standard Bifenthrin (CAPTURE 2EC) (0.04 lb/a) plus Acephate (Orthene 90S) at 0.75 lb/a against three rates of the inventive whitefly insecticide, designated an AZ-544 (4.25% active).

Pots of lantana were established in a greenhouse at the University of Arizona Maricopa Agricultural Center to provide a suitable host for the sweet potato whitefly. 180 lantana plants were seeded with a population of *Bemesea tabaci* whiteflies. Greenhouse temperatures during the establishment period ranged from 90° F. during the daytime to 60° F. at night. Nighttime temperatures were raised to 85° F. by using supplemental heating as a means of increasing the numbers of sweet potato whitefly in the greenhouse. Lantana planting were segregated into set of eight which represented a single experimental unit.

Treatments were arranged in a randomized complete block design with four replications per treatment. Each plot consisted of eight lantana plantings. Because the plantings were in close proximity to one another, a wood frame was constructed (4 ft deep by 2.5 ft high by 3 ft wide) and lined with plastic. This frame was placed over the eight plants that were to be treated with the insecticide treatments. This structure was very effective at keeping the insecticide treatments. This structure was also very effective at keeping the insecticide confined to its intended target and prevented any drift to adjacent plots.

The lantana was 12 to 14 inches tall and had completed a flowering cycle when the first insecticide treatments were applied. Prior to the application of the insecticide treatments a leaf sample was obtained from the third set of alternate leaves from the inflorescence. Egg and nymphs counts were obtained from the harvested leaf. Adult populations were determined from leaf turns during early morning hours when the adults were present on the upper one-third of the plant.

All treatments were applied by a $CO_2$ propelled sprayer equipped with a three nozzle boom, one nozzle which was centered over the plant while the remaining nozzles were mounted on swivels that were placed at the end of 6 inch drops. This nozzles arrangement and choice of nozzle (TX3) provided excellent coverage on surface as well as the underside of each leaf. 500 milliliters of the insecticide was delivered to the appropriate set of eight lantana plantings by running the boom back and forth over the plantings until 500 mls of insecticide had been exhausted on the treatment. The spray was forced into the lantana canopy with 50 lbs of pressure.

Five days after application three leaves were selected from each plant from the third set of opposite leaves from the terminal. The leaves were placed in a plastic bag and counted for egg and nymph populations per one-half square inch of leaf surface.

The second application was made 16 days after the first application. Adult whitefly populations at the time of treatment averaged about 4 to 6 whiteflies per leaf and plants exhibited some honeydew as a result of feeding from the whitefly.

The inventive whitefly insecticide, designated as AZ-544, with a formulation number 0.729 EC, was applied to lantana on a 14 days schedule for a total of 4 applications per treatment. These rates correspond to a 175:1, 125:1, 75:1 which is represented in terms of % solution below.

TABLE

The table shows the results of the tests.

| Treatment | Rate (% or lb/a) | Eggs | Nymphs | Adults |
|---|---|---|---|---|
| AZ-544 | 0.0041 | 39 | 16 | 166 |
| AZ-544 | 0.0058 | 65 | 10 | 103 |
| AZ-544 | 0.0097 | 38 | 14 | 137 |

The tests for the inventive whitefly insecticide show unexpected surprisingly good results. The inventive whitefly insecticide showed surprisingly good activity on the egg and nymphal stage. The tests also showed that the Capture/Orthene insecticide can have a toxic residual influence on the plants but the inventive whitefly insecticide AZ-544 does not appear to have any adverse residual activity to the plants following application.

The means represented in the table represents an average of 15 leaves per replication or 60 leaves per treatment. Counts per leaf were obtained by observing ½ square inch of leaf using a Bausch & Laumb Stereoscope.

Further tests were also conducted to determine if the inventive whitefly insecticide was toxic to sweet potato whiteflies, *Bemisia tabaci* (Gennadius). Whitefly populations were maintained on poinsettia plants in a greenhouse in Tucson, Arizona. Whitefly eggs were deposited on cotton leaves by placing approximately 100 adults in a clip cage attached to the underside of cotton leaves for three hours. This was replicated four times. After that time, cages and adults were removed from the leaves that were still attached to the plants.

The plants were treated with two rates of the inventive whitefly insecticide at concentrations of 1/50 and 1/100 v/v. The whitefly insecticide was applied using a hand held spray bottle. Leaves were sprayed from a bottle with constant agitation until run off. The following day, counts were made to determine the number of eggs on each leaf. Leaves were then examined at intervals ranging from 2 to 7 days. Whiteflies were counted and their stage of development was recorded. Counts continued until all the insects had either died or reached adulthood. Differences between means were examined using a Student-Newman-Kuels test at the 1% level.

The test results were unexpectedly surprisingly good. The whitefly insecticide AZ-543, at a concentration of 1/100, resulted in a crawler mortality of $95.1 \mp 1.4\%$. None of the other treatments allowed whiteflies to progress past the crawler stage (i.e., crawlers suffered 100% mortality). These mortality rates were significantly different ($P<0.01$) than rates suffered by whiteflies that were not treated ($22.4 \mp 15.3\%$).

Uses

The whitefly insecticide is particularly suited for use as a fly sprays. The whitefly insecticide can also be used as stomach poisons for leaf-eating insects and as contact insecticides for sucking insects. The whitefly insecticide may also cause physiological changes caused in the treated insect which affect reproduction of sterility or abnormal development.

Typical insects which may be controlled by the present invention are: *Bemisia tabaci* whiteflies or sweet potato whiteflies, Diptera such as mosquitos and houseflies, Homoptera such as aphids, Hemiptera such as Pyrrhocoridae and Miridae; Lepidoptera such as Pyralidae and Gelechidae, and Coleoptera such as Tenebrionidae, Chrysomelicae and Dermestidae. For example, *Pyrrhocoris apterus, Lygus hesperus, Galleria mellonella, Plodia interpuctella, Phtorimoca operculella, Tenebrio molitor, Triboleum confusm, Diabrotica duo-decimpunctata, Dermestes maculatus, Aedes aegypti* and *Musca domestica.*

The whitefly insecticide, also known as Enviro-cide Whitefly insecticide spray, is useful to control pests. When used as a spray, the user should shake the insecticide well before using. The sprayer can be held 18 inches from foliage and sprayed with circular motion. A direct spray can be used so that upper and lower leaf surfaces are contacted. The user should exercise caution on new growth and tender foliage. Fish bowls, furniture, floors and walls can be covered with paper before spraying. The spray should be applied in a manner to provide complete and uniform coverage of infested plants. The user should seek good coverage of underside of leaves and trunk or main stem. Overspraying to the point of excessive runoff, should be avoided. Treat, when pests appear and repeat at 7 to 10 day intervals, if needed.

Among the many advantages of the whitefly insecticidal composition, formulation and technology of the invention are:

1. Superior insecticide for whiteflies and other insects.
2. Safe for humans, wildlife, mammals, animals, plants, birds, and aquatic life.
3. Outstanding product performance.
4. Ecologically attractive.
5. Does not pollute the air nor contaminate the soil or water.
5. Beneficial to the environment.
6. Easy to use.
7. Cost effective.
8. Superior quality.
9. Biodegradable.
10. Reliable.
11. Efficient.
12. Effective.

Although embodiments of the invention have been shown and described, it is to be understood that various modifications and substitutions, as well as rearrangements of parts, components, and process steps, can be made by those skilled in the art without departing from the novel spirit and scope of this invention.

What is claimed is:

1. An insecticide for controlling whiteflies, mosquitoes and other pests, comprising:

an insecticidal oil-containing amide selected from the group consisting of a stomach poison for leaf-eating insects, a contact insecticide for sucking insects, a systemic insect control agent, and a fly insecticide, for controlling insects selected from the group consisting of whiteflies, spider mites, aphids, flea beetles, leaf hoppers, grasshoppers, houseflies, mosquitoes, diptera, homoptera, hemiptera, lepidoptera, coleoptera, mealybugs, rose slugs, scales, thrips, gnats, armyworms, bagworms, weevils, budworms, cankerworms, gypsy mothor, Japanese beatles, leafminers, leafrollers, pine tip moths, tent caterpillars, webworms, and leaf-eating caterpillars:

said insecticidal oil-containing amide comprising an oil selected from the group consisting of: corn oil, casteroil, palm oil, palm kernel oil, soybean oil, cottonseed oil, tall oil, lard oil, oleic oil, rape oil, linseed oil, olive oil, peanut oil, fish oil, soybean oil, sesame oil, hemp seed oil, perilla oil, styrax oil, oiticica oil, kayo oil, walnut oil, cashew oil, poppy seed oil, safflower oil, watermelon seed oil, sunflower oil, rice bran oil, pumpkin seed oil, tsubaki oil, crystalis oil, kaoliang oil, ergot oil, bone oil, shark oil, sardine oil, pike oil, herring oil, saurel oil, cod oil, cuttlefish oil, trout oil, mullet oil, tuna oil, menuke oil, menhadden oil, eel oil, whale oil, liver oil, chinawood oil, plant oil, vegetable oil and animal oil;

said insecticidal oil-containing amide comprising monoethanolamide; and an insecticidal surfactant; and said insecticidal oil-containing amide and said insecticidal surfactant cooperating with each other to provide an insect-resistant protective agents for protecting plants selected from the group consisting of cotton, watermelon, cantaloupe, vegetables, alfalfa, wheat, carrot, peanuts, citrus, eggplants, honeydew melons, broccoli, cabbage, lettuce, celery, peppers, squash, sweet potatoes, cauliflower, corn, tomatoes, cucumbers, fruits, sweet potatoes, ornamental, poinsettias, African violets, azaleas, begonias, camellias, dahlias, dogwood, roses, carnations, chrysanthemums, geraniums, gladiolus marigolds, shrubs, trees and grass.

2. An insecticide in accordance with claim 1 wherein said insecticidal oil-containing amide comprises a monoethanolamide comprising at least one member selected from the group consisting of cottonseed oil amide and tall oil amide and said insecticidal surfactant and said insecticidal oil amide cooperate with each other to provide a biodegradable insecticide.

3. An insecticide in accordance with claim 1 wherein said insecticidal oil-containing amide is a reaction product of a fatty acid or a fatty acid ester and an amine comprising monoethanolamine.

4. An insecticide in accordance with claim 1 wherein said monoethanolamide comprises by weight;
from about 25% to about 40% cottonseed oil amide;
from about 10% to about 35% coconut oil amide; and
from about 2% to about 15% tall oil amide; and said insecticidal surfactant is selected from the group consisting of: a nonionic surfactant, an avionic surfactant, a cationic surfactant, an ampholytic surfactant and a zwitterionic surfactant.

5. An insecticide in accordance with claim 1 wherein said surfactant comprises a wax-stripping surfactant for stripping wax and oil from insects.

6. An insecticide in accordance with claim 1 wherein said surfactant comprises an insect-suffocating wetting agent to suffocate insects.

7. An insecticide in accordance with claim 1 wherein said surfactant comprises a penetrate for penetrating insect eggs and nymphs.

8. An insecticide in accordance with claim 1 including an aqueous carrier for carrying said amide and surfactant to insects.

9. An insecticide in accordance with claim 1 including a non-aqueous hydrophobic carrier comprising a member selected from the group consisting of: hydrocarbon oil, mineral oil, silica, talc, resin, xylene, benzene, toluene, acetone, methane, butane, propane, acetylene, ethane, ethylene, butane, butylene, pentane, a petroleum based liquid, cottonseed oil, vegetable oil, plant oil, seed oil, nut oil, fish oil, and animal oil.

10. An insecticide for controlling whiteflies and other insects, comprising:

an environmental insecticidal concentrate which can safely contact humans and plants, said concentrate comprising by weight from about 1% to about 50% nonionic surfactants comprising a phenol ethoxylate selected from the group consisting of a condensate product of ethylene oxide and an alkyl phenol or an aliphatic alcohol, and a condensate product of ethylene oxide and an alkyl phenol or an aliphatic alcohol;

oil-containing alkanol amides comprising monoethanolamide;

said monoethanolamide comprising by weight
from about 1% to about 50% cottonseed oil amide;
from about 1% to about 40% coconut oil amide; and
from about 1% to about 20% tail oil amide.

11. An insecticide in accordance with claim 10 wherein said concentrate further comprises by weight:

from about 1% to about 5% chelating agent;

from about 1% to 10% viscosity control agent; and from about 1% to about 10% free alkanol amine comprising at least one olamine-containing compound selected from the group consisting of monopropanolamine, dipropanolamine, isopropanolamine, monobutanolamine, monoisobutanolamine, dibutanolamine, monopentanolamine, monohexanolamine, dihexanolamine, monoctanolamine, dioctanolamine, and cyclohexanolamine.

12. An insecticide in accordance with claim 10 further including water and wherein the ratio of water to said concentrate ranges from about 10,000:1 to about 200:1.

13. An insecticide for controlling whiteflies and other insects, comprising:

a biodegradable insecticidal concentrate which is nontoxic to humans and plants, said concentrate comprising by weight from about 25% to about 40% nonionic surfactants comprising a member selected from the group consisting of nonylphenol ethoxylate and octylphenol ethoxylate;

oil-containing ethanol amides comprising monoethanolamide;

said monoethanolamide comprising by weight
from about 25% to about 40% cottonseed oil amide;
from about 10% to about 35% coconut oil amide;
from about 2% to about 15% tall oil amide;
from about 2% to about 8% viscosity control agent;
from about 1% to about 4% chelating agent; and
from about 2% to about 8% excess hydroxyalkylamine comprising at least one member selected from the group consisting of monoethanolamine, diethanolamine and triethanolamine.

14. An insecticide in accordance with claim 13 wherein:

said oil-containing amides are reaction products of hydroxyalkylamines and cottonseed oil, coconut oil and tall oil, the ratio of said oils to said hydroxyalkylamines ranging from about 2.5:1 to about 1.5:1; and said nonionic surfactant comprising a reaction product of ethylene oxide and a phenol comprising a member selected from the group consisting of nonyphenol and octylphenol, and the ratio of said phenol to said ethylene oxide ranging from about 2:20 to about 4:16.

15. An insecticide in accordance with claim 13 further including water and wherein the ratio of water to said concentrate ranges from about 6000:1 to about 500:1.

16. An insecticide in accordance with claim 13 comprising by weight:

from about 32% to about 35% nonionic surfactants;

from about 32% to about 35% cottonseed oil amide;

from about 15% to about 28% coconut oil amide;

from about 5% to about 10% tall oil amide;

from about 3% to about 5% viscosity control agent;

from about 2% to about 3% chelating agent; and from about 3% to about 5% excess hydroxyalkylamines.

17. An insecticide in accordance with claim 16 further including water and wherein the ratio of water to said concentrate ranges from about 1200:1 to about 800:1.

18. An insecticide in accordance with claim 16 wherein:

said viscosity control agent comprises sodium xylene sulfonate;

said chelating agent comprises a tetrasodium salt of ethylene diamine tetracedic acid; and said hydroxyalkylamines comprise monoethinolamine.

* * * * *